United States Patent
Chakrabarty et al.

(10) Patent No.: US 10,654,792 B2
(45) Date of Patent: May 19, 2020

(54) CARBOXYLIC ACID ESTER PRODRUG INHIBITORS OF MEK

(71) Applicant: DUQUESNE UNIVERSITY OF THE HOLY GHOST, Pittsburgh, PA (US)

(72) Inventors: Suravi Chakrabarty, Pittsburgh, PA (US); Darlene Monlish, Pittsburgh, PA (US); Patrick Flaherty, Pittsburgh, PA (US); Jane E. Cavanaugh, Pittsburgh, PA (US); Sneha Potdar, Pittsburgh, PA (US)

(73) Assignee: DUQUESNE UNIVERSITY OF THE HOLY SPIRIT, Pittsburgh, PA (US)

(*) Notice: Subject to any disclaimer, the term of this patent is extended or adjusted under 35 U.S.C. 154(b) by 0 days.

(21) Appl. No.: 15/383,635

(22) Filed: Dec. 19, 2016

(65) Prior Publication Data
US 2017/0096388 A1   Apr. 6, 2017

Related U.S. Application Data

(62) Division of application No. 14/081,426, filed on Nov. 15, 2013, now Pat. No. 9,556,112.

(60) Provisional application No. 61/726,914, filed on Nov. 15, 2012.

(51) Int. Cl.
    C07C 227/10   (2006.01)
    C07C 229/58   (2006.01)

(52) U.S. Cl.
    CPC .......... *C07C 227/10* (2013.01); *C07C 229/58* (2013.01)

(58) Field of Classification Search
    None
    See application file for complete search history.

(56) References Cited

U.S. PATENT DOCUMENTS

| | | |
|---|---|---|
| 7,858,784 B2 | 12/2010 | Buchwald et al. |
| 2004/0039208 A1 | 2/2004 | Chen et al. |
| 2004/0054172 A1* | 3/2004 | Barrett ............... C07D 261/02 544/59 |
| 2005/0004186 A1 | 1/2005 | Barrett et al. |
| 2005/0137263 A1 | 6/2005 | Rewcastle et al. |
| 2005/0176820 A1 | 8/2005 | Barrett et al. |
| 2009/0105474 A1 | 4/2009 | Yokotani et al. |
| 2009/0156576 A1* | 6/2009 | Aay .................... C07D 205/06 514/210.18 |

FOREIGN PATENT DOCUMENTS

WO   WO-2009036020 A1 *   3/2009  ........... C07C 259/10

OTHER PUBLICATIONS

Hattori ("Convenient Synthesis of Triarylamines via Ester-Mediated Nucleophilic Aromatic Substitution" Synthesis, 1996, p. 514-518).*

Nishio (Synthesis of Acridone Derivatives Using Polymer-Supported Palladium and Scandium Catalysts: J. Comb. Chem. 2006, 8, p. 459-461).*
Belfield ("Recent Synthetic Advances in the Nucleophilic Amination of Benzenes" Tetrahedron, 55, 1999, p. 11399-11428).*
Chupakhin ("Recent Advances in the field of nucleophilic aromatic substitution of hydrogen" Tetrahedron Letters, 2016, p. 2665-2672).*
Charushin ("Nucleophilic aromatic substitution of hydrogen and related reactions" Mendeleev Communications, 2007, 17, p. 249-254).*
Li ("Sc(OTf)3-Catalyzed Dehydrogenative Cyclization for Synthesis of N-Methylacridones" Organic Letters, 2013, vol. 15, No. 8, p. 1794-1797, including Si p. S1-S54) (Year: 2013).*
Wolf ("Regioselective Copper-Catalyzed Amination of Bromobenzoic Acids Using Aliphatic and Aromatic Amines" J. Org. Chem. 2006, 71, p. 3270-3273) (Year: 2006).*
Tecle et al., "Beyond the MEK-pocket: Can current MEK kinase inhibitors be utilized to synthesize novel type III NCKIs? Does the MEK-pocket exist in kinases other than MEK?", Bioorganic & Medicinal Chemistry Letters, Jan. 1, 2009, pp. 226-229, vol. 19, No. 1.
Davis et al., "Utilization of Lithium Amide in the Synthesis of N-Arylanthranilic Acids and N-Arylanthranilamides", Organic Process Research & Development, Jan. 1, 2005, pp. 843-846, vol. 9, No. 6.
Juby et al., "Preparation and Antiinflammatory Properties of Some 5-(2-Anilinophenyl)tetrazoles", Journal of Medicinal Chemistry, American Chemical Society, Jan. 1, 1968, pp. 111-117, vol. 11, No. 1.
Ullmann, "Ueber Arylanthranilsauren", Justus Liebigs Annalen Der Chemie, Jan. 1, 1907, pp. 312-358, vol. 355, No. 3.

(Continued)

*Primary Examiner* — Amy C Bonaparte
(74) *Attorney, Agent, or Firm* — Eckert Seamans Cherin & Mellott, LLC; Carol A. Marmo

(57) ABSTRACT

The invention generally relates to compounds having structure I:

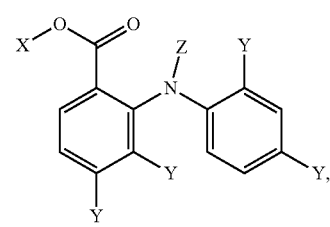

X = alkyl, aryl, hetaryl
Y = halogen, H
Z = akyl, H wherein x represents alkyl, aryl or het-aryl, each of y independently represents hydrogen or halogen and z represents hydrogen or alkyl. Further, said compounds are inhibitors of MEK 1, 2 and 5. Furthermore, the invention includes methods of making said compounds, compositions including said compounds and uses for inhibiting MEK 1, 2 and 5.

7 Claims, No Drawings

(56) References Cited

OTHER PUBLICATIONS

European Patent Office, Extended European Search Report for European Application No. 13855132.0, dated Jun. 1, 2016.
Lavoie et al., "Bioisosterism: A Rational Approach in Drug Design", Chem. Rev. 1996, pp. 3147-3176, vol. 96, No. 8.

\* cited by examiner

CARBOXYLIC ACID ESTER PRODRUG INHIBITORS OF MEK

This application is a divisional of, and claims the benefit of priority to, U.S. Ser. No. 14/081,426, entitled "Carboxylic Acid Ester Prodrug Inhibitors of MEK" filed on Nov. 15, 2013, which claims priority under 35 U.S.C. § 119(e) from U.S. provisional patent application No. 61/726,914, entitled "Carboxylic Acid Ester Prodrug Inhibitors of MEK for Macular Degeneration" and filed on Nov. 15, 2012, the contents of which are incorporated herein by reference.

FIELD OF THE INVENTION

The invention generally relates to novel compounds and, in particular, compounds of inhibitors of MAPK kinases 1, 2 and 5 (MEK 1, 2 and 5), methods of making said compounds, and their use in inhibiting MEK 1, 2 and 5 activity.

BACKGROUND OF THE INVENTION

There are known in the art various MEK1/2 inhibitors, such as but not limited to diphenyl anilines. In some instances, these compounds were discovered for use in developing new anticancer agents.

The Mitogen-Activated Protein-Kinase (MAPK) signaling cascade is a complex web of kinases that connects external and internal stimuli to effect modification of cell energy levels and movement involving the cytoskeleton. Consequently the MAPK signaling cascade was previously known as the microtubule-associated protein kinase signaling cascade.

Since the majority of prior art addresses the development of MEK1/2 inhibitors, there is a need in the art to develop compounds that address MEK5 inhibition and, compounds that address MEK1/2 inhibition and MEK5 inhibition are particularly advantageous.

SUMMARY OF THE INVENTION

In one aspect, the invention provides a compound of structure I:

I

X = alkyl, aryl, hetaryl
Y = halogen, H
Z = akyl, H wherein, X represents alkyl, aryl or hetaryl, each of Y independently represents hydrogen or halogen, and Z represents hydrogen or alkyl.

The compound of structure I can be an inhibitor of MEK1, 2 and 5.

In certain embodiments, the invention provides a composition that includes a therapeutically effective amount of the compound having structure I.

In another aspect, the invention provides one of the following methods of preparing the compound of structure I:

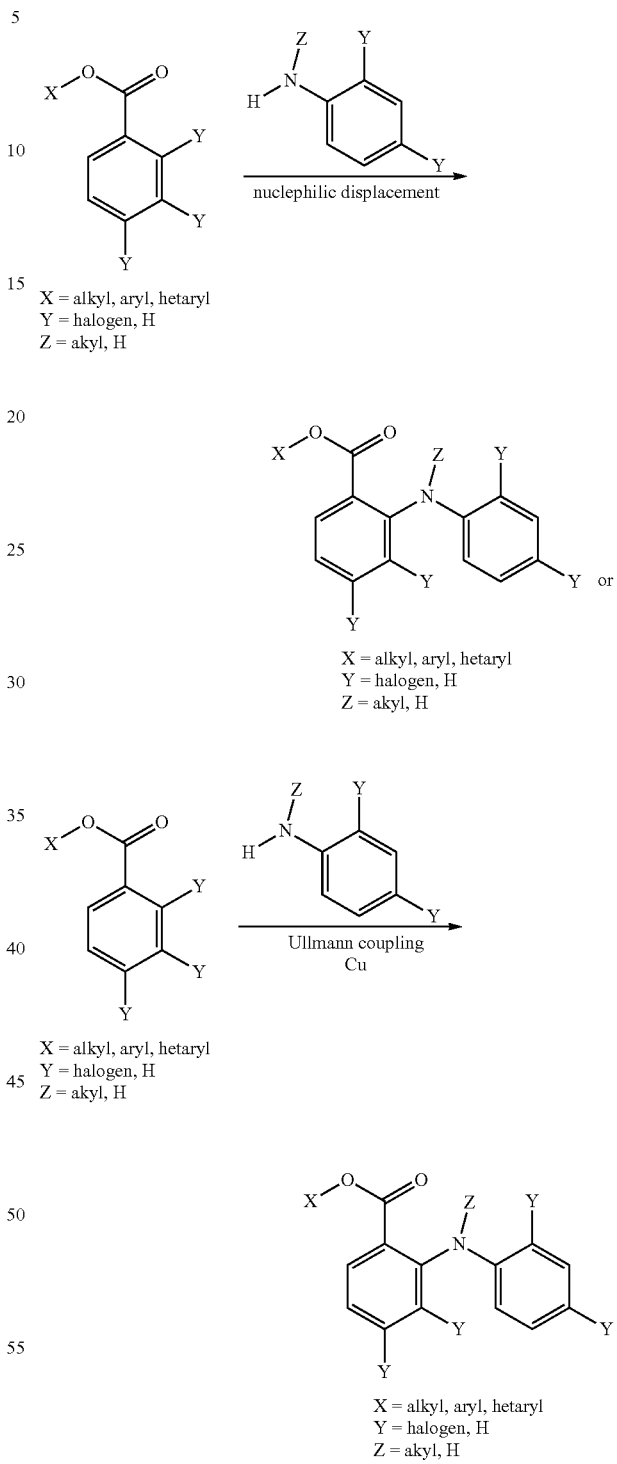

X = alkyl, aryl, hetaryl
Y = halogen, H
Z = akyl, H

DETAILED DESCRIPTION OF PREFERRED EMBODIMENTS

The invention relates to compounds having the following structure I:

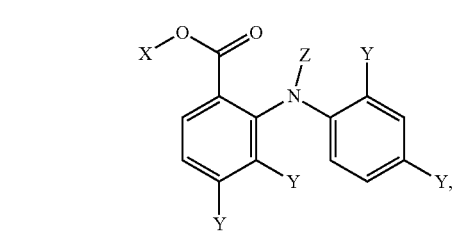

X = alkyl, aryl, hetaryl
Y = halogen, H
Z = akyl, H wherein, X represents alkyl, aryl or hetaryl, each of Y independently represents hydrogen or halogen and Z represents hydrogen or alkyl.

In certain embodiments, alkyl can include but is not limited to methyl, ethyl, propyl, and butyl. Further, in certain embodiments, halogen can include but is not limited to fluorine, chlorine, bromine and iodine.

The compounds of the invention are inhibitors of mitogen-activated protein kinase (MAPK) 1, 2 and 5 (MEK 1, 2 and 5) Further, the invention includes methods of making said compounds, and their use in inhibiting MEK 1, 2 and 5 activity.

Furthermore, the invention includes compositions that include a therapeutically effective amount of the compound having structure I to administer to a patient. As used herein, the term "therapeutically effective amount" means an amount or dosage such that, when administered in a physiologically tolerable composition, is sufficient to achieve an effective systemic concentration or local concentration in tissue to elicit a response in the tissue, system or individual to which it was administered. The term "administering" and the like means to administer a compound or composition systemically or locally, as directly into or onto a target tissue, to a patient whereby the compound or composition positively impacts the tissue to which it is targeted. The compound or composition may be administered by injection, topical administration and oral administration or by other methods alone or in combination with other known techniques. The term "inhibit" or the like includes the administration of a compound or composition to at least partially prevent symptoms, a disease, condition or disorder.

Without intending to be bound by any theory, it is believed that a carboxylate can make an ionic interaction with an arginine in the proximity of the proposed allosteric binding site. A similar arginine residue exists in MEK1/2 although at a slightly different location. Further, it is believed that a carboxylic ester delivers a carboxylic acid across a cellular membrane as a prodrug to deliver a metabolically released active MEK inhibitor. The carboxylic acid released is similar to carboxylic acid NSAIDS.

In certain embodiments, the compounds of the invention can be made in accordance with the following preparation schematic A:

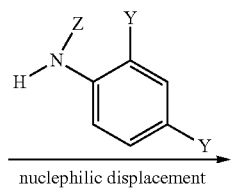

X = alkyl, aryl, hetaryl
Y = halogen, H
Z = akyl, H

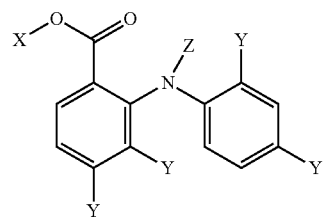

X = alkyl, aryl, hetaryl
Y = halogen, H
Z = akyl, H

In certain other embodiments, the compounds of the invention can be made in accordance with the following preparation schematic B:

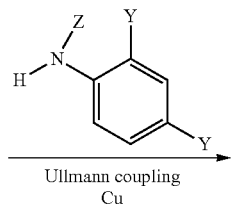

X = alkyl, aryl, hetaryl
Y = halogen, H
Z = akyl, H

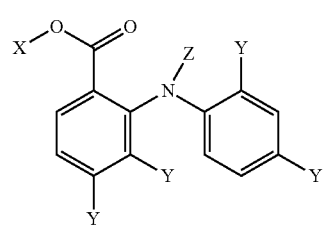

X = alkyl, aryl, hetaryl
Y = halogen, H
Z = akyl, H

EXAMPLES

Chemical Synthesis/Biological Testing of
Carboxylic Acid-Based Inhibitors of MEK 5

TABLE I

| Structure | registration ID | cellular pERK1/2 decrease (%) | cellular pERK5 decrease (%) |
|---|---|---|---|
| 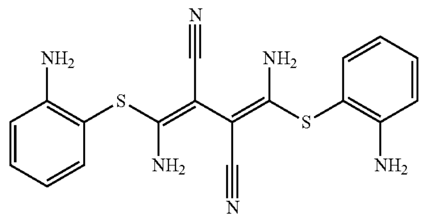 [SMILES: N#CC(=C(/N)Sc1ccccc1N)/C(C#N)=C(\N)Sc1ccccc1N] | U0126 | 99.72 | 0.28 |
| 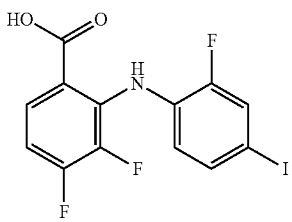 [SMILES: O=C(O)c1ccc(F)c(F)c1Nc1ccc(I)cc1F] | SC-1-148 (SC-1-180) | 98.5 | 20.1 |
| 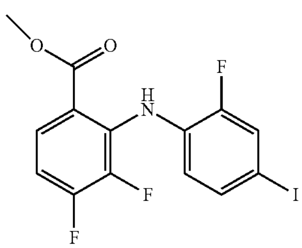 [SMILES: COC(=O)c1ccc(F)c(F)c1Nc1ccc(I)cc1F] | SC-1-72 Ester | 98.5 | 20.1 |
| 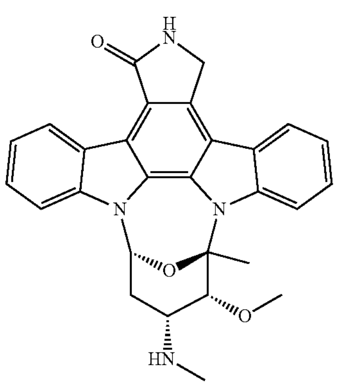 [SMILES: CN[C@@H]1C[C@H]2O[C@@](C)([C@@H]1OC)n1c3ccccc3c3c4c(c5c6ccccc6n2c5c31)C(=O)NC4] | staurosporine | 98.93 | 13 |
| 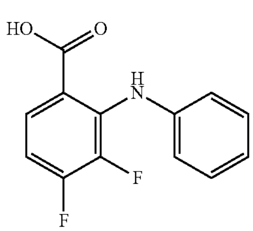 [SMILES: O=C(O)c1ccc(F)c(F)c1Nc1ccccc1] | SC-1-175 | 64.4 | 2.1 |

The above compounds identified in Table I were tested in a cellular assay and demonstrated the activity listed for cellular MEK1/2, MEK5 phsophorylation of their related ERK following induction by EFG and determined by western blot analysis. Compounds staurosporine and U0126 are included as standards.

Experimental: Chemical Synthesis

The chemical synthesis of the following compounds followed traditional nucleophilc displacements of a halogen by attack of an analide to give the desired compounds. In some instances, it was necessary to use an Ulmann coupling strategy.

3,4-Difluoro-2-((2-fluoro-4-iodophenyl)amino)benzoic Acid (SC-1-148 Acid)

A 250 mL round bottom flask was charged with 2-fluoro-4-iodoaniline, (73; 2.38 g, 10.05 mmol), 2,3,4-trifluorobenzoic acid, (74; 1.8 g, 10.225 mmol), and 30 mL of anhydrous THF. The reaction mixture was cooled with an ice-bath to 0° C. and $LiNH_2$ (561.2 mg, 24.45 mmol) was added in portions 3 portions over 10 min. The reaction was then warmed to 58° C. and stirred for 12 h. 1 N HCl was then added to the reaction mixture at 0° C. to obtain a final pH of 1.0 (red to pHydrion paper). The reaction mixture was extracted three times with 10 mL portions of $Et_2O$, washed three times with 5 mL portions of 1 N HCl, washed with NaCl (aq, sat) and dried over $Na_2SO_4$. The extract was decanted and the solvent was removed under reduced pressure. The crude product was isolated on $SiO_2$ using hexane/EA and provided 2.11 g (53%) of a white solid. mp: 199.0-200.1° C. (lit: 200-201° C.). $SiO_2$ TLC $R_f$ 0.51 (2:1 hexane/EA). $^1H$ NMR (MeOD-$d_4$): δ 7.86 (m, 1 H), 7.46 (d, J=1.6 Hz, 1 H), 7.38 (d, J=1.6 Hz, 1 H), 7.18 (m, 1 H, OH), 6.86 (m, 1 H), 6.72 (m, 1 H), 2.31 (m, 1 H, NH). Anal Calcd for $C_{13}H_7F_3INO_2$: C, 39.72; H, 1.79; N, 3.56. Found: C, 39.41; H, 1.91; N, 3.52.

SC-1-14 Acid (Ullmann Coupling)

A microwave reactor tube was charged with ortho-iodo benzoic acid (496 mg, 2 mmol), 2-fluoro-4-iodo aniline (237 mg, 1 mmol), $K_2CO_3$ (416 mg, 3 mmol), CuI (200 mg, 1.04 mmol) and 5 mL DMF/$H_2O$ (9:1). The reaction was subjected to 300 Watt microwave irradiation with the internal temperature maintained at 100° C. for 2 h. After completion of the reaction was observed by TLC, 1 N HCl (~4 mL) was added to the reaction mixture to obtain a final pH of 6.0. The solvent was then removed under reduced pressure. The crude compound was isolated on $SiO_2$ using hexane/EA to give 217 mg (61%) of white solid; mp: 176.6-177.0° C.

SC-1-24 Amide

A dry 100 mL round bottom flask was charged with SC-1-14, (140 mg, 0.39 mmol) and 5 mL of DCM. The reaction mixture was cooled on ice-bath to 0° C. 100 μL of anhydrous DMF was added followed by dropwise addition of oxalyl chloride (70 μL, 0.8 mmol) over 2 min at 0° C. The reaction was stirred at 23° C. for 2 h. The solvent was then removed under reduced pressure. The crude product was dissolved in 5 mL of DCM and the appropriate amine (0.5 mL, 11.5 mmol) was added neat at 23° C. The reaction was stirred at 23° C. for 2 h; completion of reaction was determined by TLC. A mixture of 10 mL of DCM and 5 mL of 5% $Na_2CO_3$ was added and the resultant mixture was extracted with DCM, washed with NaCl (aq, sat), and dried over $Na_2SO_4$. The extract was decanted and then the solvent was removed under reduced pressure and water chased with toluene. The crude product was isolated on $SiO_2$ using EA/0.5% TEA/10% ethanol and recrystallised from HCl salt (ethereal HCl) to give 20 mg (12%) of off-white powder. mp: 217.2-217.5° C.

SC-1-39 Acid

A microwave reactor tube was charged with ortho-iodo benzoic acid (496 mg, 2 mmol), aniline (0.45 mL, 4 mmol), $K_2CO_3$ (832 mg, 6 mmol), CuI (400 mg, 2.08 mmol) and 10 mL DMF/$H_2O$ (9:1). The reaction was subjected to 300 Watt microwave irradiation with the internal temperature maintained at 100° C. for 1 h. After completion of the reaction was observed by TLC, 1 N HCl (~9 mL) was added to the reaction mixture to obtain a final pH of 6.0. The solvent was then removed under reduced pressure and water chased with toluene. The crude compound was isolated on $SiO_2$ using hexane/EA and recrystallised from toluene to give 267 mg (63%) of white solid; mp: 176.6-177.0° C.

SC-1-175 Acid

A 250 mL round bottom flask was charged with aniline (0.57 mL, 5.7 mmol), 2,3,4-trifluorobenzoic acid, (1 g, 5.7 mmol), and 15 mL of anhydrous THF. The reaction mixture was cooled with an ice-bath to 0° C. and $LiNH_2$ (327 mg, 14.25 mmol) was added in portions 2 portions over 10 min. The reaction was then warmed to 58° C. (external temperature) and stirred for 7 h. 1 N HCl was then added to the reaction mixture at 0° C. to obtain a final pH of 1.0 (red to pHydrion paper). The reaction mixture was extracted three times with 5 mL portions of $Et_2O$, washed three times with 5 mL portions of 1 N HCl, washed with NaCl (aq, sat) and dried over $Na_2SO_4$. The extract was decanted and the solvent was removed under reduced pressure. The crude product was isolated on $SiO_2$ using hexane/EA and provided 606 mg (44%) yellow crystals. mp: 162.1-162.6° C. $SiO_2$ TLC $R_f$ 0.61 (2:1 hexane/EA).

Experimental: Biological Testing

Western Blot Analysis of Potential MEK-5 Inhibitors

The MDA-MB-231 triple negative breast cancer cell line was pretreated with compounds (10 μM) for 30 min followed by stimulation with epidermal growth factor (EGF, 50 ng/mL) for 15 min. Vehicle-treated cells were pretreated with DMSO for 30 min prior to EGF stimulation for 15 min. Protein visualization and quantification analysis was performed using LI-COR Odyssey Imager.

*$P<0.05$ vs. Vehicle, one-way ANOVA followed by Tukey-Kramer test (n=3)

While the invention has been illustrated by the description of embodiments thereof, and while the embodiments have been described in considerable detail, it is not intended to restrict or in any way limit the scope of the appended claims to such detail. Additional advantages and modifications will be readily apparent to those skilled in the art. The invention in its broader aspects is therefore not limited to the specific details, representative system and method, and illustrate examples shown and described. Accordingly, departures may be made from such details without departing from the scope or spirit of the invention.

The invention claimed is:

1. A method for preparing a compound of structure Ia or structure Ib:

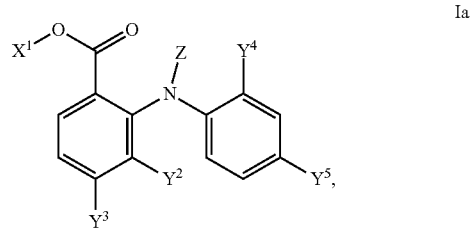

-continued

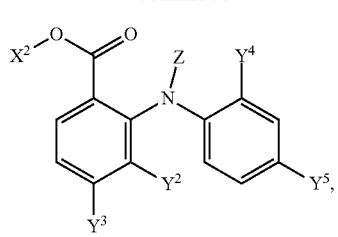
Ib the method comprising a reaction scheme selected from the group consisting of the following:

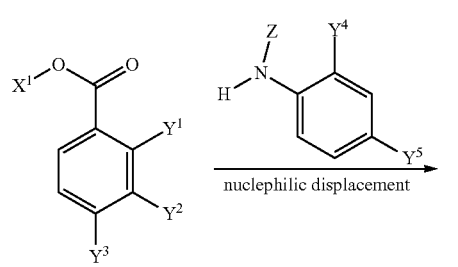
Ia

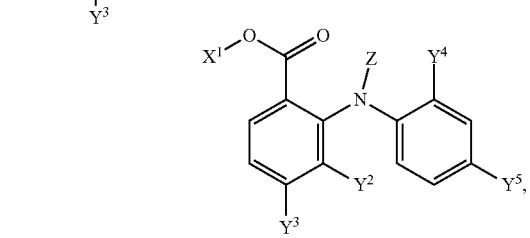
Ib

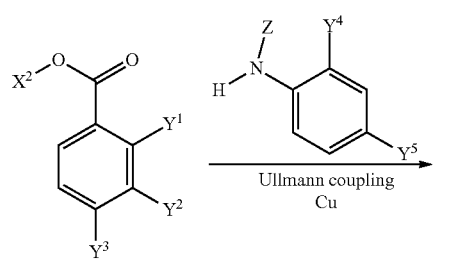

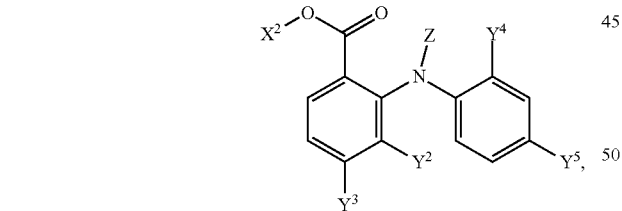

wherein: $X^1$ is hydrogen, $X^2$ is hydrogen, alkyl, aryl or hetaryl, $Y^1$ is halogen, Z is hydrogen or alkyl, and
$Y^4$ is fluorine, $Y^5$ is iodine, and $Y^2$ and $Y^3$ are hydrogen, or
$Y^4$ and $Y^5$ are hydrogen, and $Y^2$ and $Y^3$ are halogen.

2. The method of claim 1, wherein $Y^4$ and $Y^5$ are hydrogen and $Y^2$ and $Y^3$ are fluorine.

3. The method of claim 1, wherein $Y^4$ is fluorine, $Y^5$ is iodine, and $Y^2$ and $Y^3$ are hydrogen.

4. A method for preparing an inhibitor of mitogen-activated protein kinase 1, 2 and 5, of structure Ia or structure Ib:

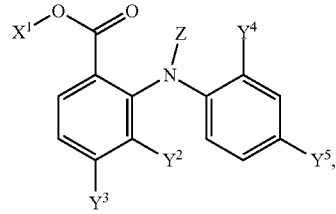
Ia

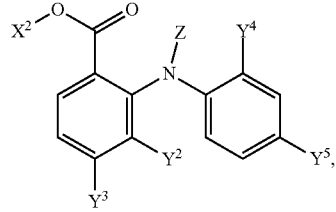
Ib the method comprising a reaction scheme selected from the group consisting of the following:

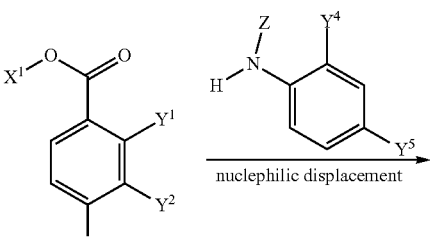
Ia

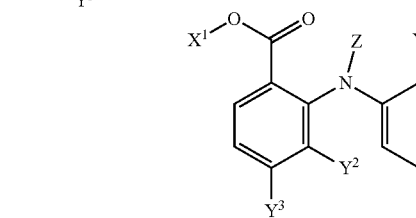
and

Ib

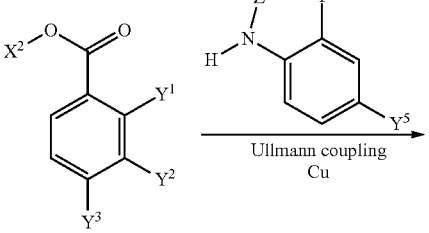

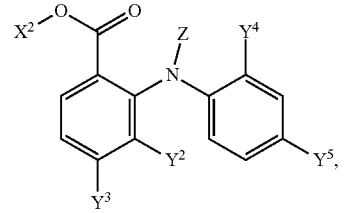

wherein: $X^1$ is hydrogen, $X^2$ is hydrogen, alkyl, aryl or hetaryl, $Y^1$ is halogen, Z is hydrogen or alkyl, and
$Y^4$ is fluorine, $Y^5$ is iodine, and $Y^2$ and $Y^3$ are hydrogen, or
$Y^4$ and $Y^5$ are hydrogen, and $Y^2$ and $Y^3$ are halogen.

5. The method of claim 4, wherein $Y^4$ and $Y^5$ are hydrogen and $Y^2$ and $Y^3$ are fluorine.

6. The method of claim 4, wherein $Y^4$ is fluorine, $Y^5$ is iodine, and $Y^2$ and $Y^3$ are hydrogen.

7. The method of claim 4, wherein $Y^1$ and $Y^4$ are fluorine, $Y^5$ is iodine, and $Y^2$ and $Y^3$ are hydrogen.

* * * * *